United States Patent
Griffin

(10) Patent No.: US 10,639,102 B2
(45) Date of Patent: May 5, 2020

(54) MAINTENANCE OF A STEAM BUBBLE DURING SURGICAL ABLATION

(71) Applicant: InnovaQuartz LLC, Phoenix, AZ (US)

(72) Inventor: Stephen E. Griffin, Peoria, AZ (US)

(*) Notice: Subject to any disclaimer, the term of this patent is extended or adjusted under 35 U.S.C. 154(b) by 0 days.

(21) Appl. No.: 15/969,849

(22) Filed: May 3, 2018

(65) Prior Publication Data
US 2019/0336216 A1 Nov. 7, 2019

(51) Int. Cl.
| | |
|---|---|
| A61B 18/22 | (2006.01) |
| A61B 18/00 | (2006.01) |
| A61B 18/20 | (2006.01) |
| A61B 18/26 | (2006.01) |

(52) U.S. Cl.
CPC .............. *A61B 18/22* (2013.01); *A61B 18/26* (2013.01); *A61B 2018/00577* (2013.01); *A61B 2018/206* (2013.01); *A61B 2018/2222* (2013.01)

(58) Field of Classification Search
CPC .. A61B 2018/00577; A61B 2018/1807; A61B 2018/208; A61B 18/24; A61B 18/201; A61B 18/22
See application file for complete search history.

(56) References Cited

U.S. PATENT DOCUMENTS

| | | | |
|---|---|---|---|
| 4,772,302 A * | 9/1988 | Abe ................. | C03B 37/01446 65/397 |
| 5,246,436 A | 9/1993 | Rowe | |
| 5,321,715 A * | 6/1994 | Trost ...................... | A61B 18/24 219/121.61 |
| 5,632,739 A * | 5/1997 | Anderson .............. | A61B 18/24 606/15 |
| 5,776,127 A | 7/1998 | Anderson et al. | |
| 6,282,349 B1 * | 8/2001 | Griffin ................. | G02B 6/3813 385/81 |
| 6,414,980 B1 * | 7/2002 | Wang ..................... | H01S 3/117 372/92 |
| 6,554,824 B2 * | 4/2003 | Davenport ............. | A61B 18/22 606/3 |
| 6,953,458 B2 | 10/2005 | Loeb | |
| 6,998,567 B2 | 2/2006 | Yeik | |
| 7,063,694 B2 * | 6/2006 | Nahen .................... | A61B 18/22 128/898 |
| 7,359,601 B2 | 4/2008 | Loeb | |
| 8,409,176 B2 * | 4/2013 | Cecchetti ............... | A61B 18/26 606/2 |

(Continued)

OTHER PUBLICATIONS

Zhang et al., "Continuous Cavitation Designed for Enhancing Radiofrequency Ablation via a Special Radiofrequency Solidoid Vaporization Process", ACS Nano. Feb. 23, 2016;10(2):2549-58.*

(Continued)

*Primary Examiner* — Michael W Kahelin
*Assistant Examiner* — Sana Sahand
(74) *Attorney, Agent, or Firm* — Yakov Sidorin; Quarles & Brady LLP; Jonathan Goodman

(57) ABSTRACT

A surgical method and tool for establishing a steam bubble between a fiber tip and a surgical target. The device and process capable of maintaining the steam bubble by providing a low-power, continuous-wave laser emission. Furthermore, the method and tool capable of delivering to the surgical target through the steam bubble a therapeutic laser emission providing ablation of the surgical target.

20 Claims, 5 Drawing Sheets

(56) References Cited

U.S. PATENT DOCUMENTS

| | | | |
|---|---|---|---|
| 8,657,811 B2* | 2/2014 | Arai | A61B 1/015 |
| | | | 128/898 |
| 8,876,810 B2 | 11/2014 | Neuberger | |
| 8,926,601 B2* | 1/2015 | Neuberger | A61B 18/22 |
| | | | 606/15 |
| 8,995,052 B1* | 3/2015 | Knappe | H01S 3/11 |
| | | | 359/341.3 |
| 9,662,173 B1* | 5/2017 | Griffin | A61B 18/24 |
| 9,678,275 B1* | 6/2017 | Griffin | G02B 6/3624 |
| 9,895,196 B2* | 2/2018 | Waisman | A61B 18/22 |
| 2010/0137847 A1* | 6/2010 | Cecchetti | A61B 18/26 |
| | | | 606/2.5 |
| 2010/0286672 A1* | 11/2010 | Walker | A61B 17/3211 |
| | | | 606/3 |
| 2013/0084544 A1* | 4/2013 | Boutoussov | A61M 31/00 |
| | | | 433/215 |
| 2013/0138033 A1* | 5/2013 | Frullini | A61N 5/0613 |
| | | | 604/20 |
| 2016/0135892 A1* | 5/2016 | Yu | A61B 18/24 |
| | | | 606/3 |
| 2017/0027645 A1* | 2/2017 | Ben Oren | A61B 6/00 |
| 2017/0036253 A1* | 2/2017 | Lukac | B23K 26/1224 |
| 2017/0135765 A1* | 5/2017 | Griffin | A61B 18/22 |
| 2017/0354464 A1* | 12/2017 | Waisman | A61B 18/22 |
| 2018/0206918 A1* | 7/2018 | Waisman | A61B 18/22 |

OTHER PUBLICATIONS

Aldoukhi, A.H. et al. Thermal Response to High-Power Holmium Laser Lithtripsy, J. Endourology, 2017, 31(2), 1308-1313.

De Boer, A. et al. Moving heat source in a confined channel: Heat transfer and boiling in endovenous laser ablation of varicose veins, Int. J.Heat Mass Trans. 2017, 113, 153-165.

Elhilali, M.M., et al. Use of the Moses Technology to Improve Holmium Laser Lithotripsy Outcomes: A Preclinical Study, J. Endourology 2017, 31(6), 598-604.

Isner, J.M. et al. Mechanism of Laser Ablation in an Absorbing Fluid Field, Lasers Surg. Med. 1988, 8, 543-554.

Laserent, Comparison of Holmium Yag lasers: 250ms Vs 350ms Vs 350ms "Double Pulse" lasers. LASErent promotional flier, 2010.

Zhang, Y. et al. Self-focusing effect of annular beams propagating in the atmosphere, Optics Exp. 2017, 25(18), 21329-21341.

* cited by examiner

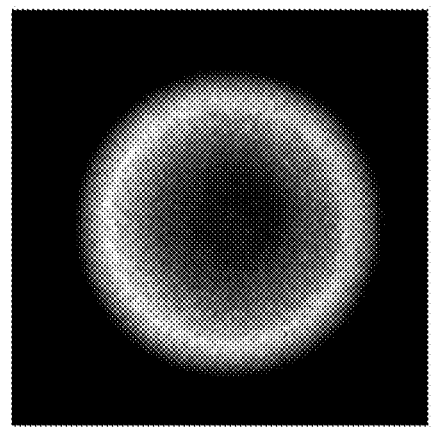
FIG. 4C
High Angle Launch (>15°)
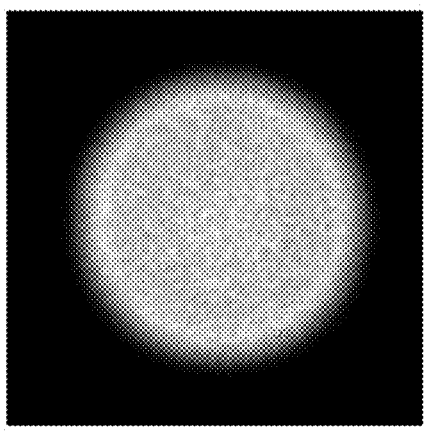
FIG. 4B
Standard Launch, Tortured Fiber
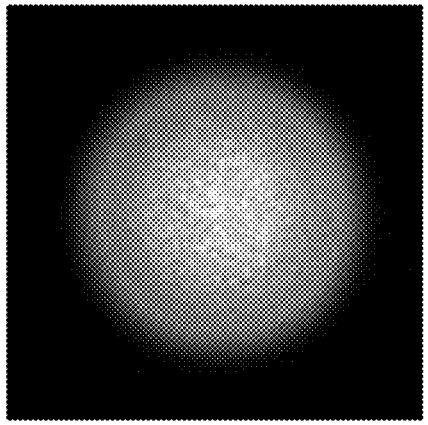
FIG. 4A
Standard Launch, Relaxed Fiber
FIG. 4

MAINTENANCE OF A STEAM BUBBLE DURING SURGICAL ABLATION

FIELD OF THE INVENTION

Embodiments of the present invention generally relate to laser energy generators intended for fragmenting or ablating urinary, biliary and salivary calculi and vaporization, excision, incision, ablation and coagulation of soft tissues using infrared wavelengths.

BACKGROUND

Absorption of laser energy by water is the basis of laser to tissue interaction of infrared lasers such as holmium (2080 nm to 2140 nm) and thulium (1900 nm to 2000 nm) FIG. 1. Within endosurgical techniques, surgical fields are also water based (e.g. saline or ringers). Laser energy is absorbed strongly within any gap between the laser fiber exit aperture and the tissue. In pulsed laser techniques, the first portion of each laser pulse is spent in boiling water, producing a steam bubble referred to as a "Moses bubble" in the field of art. Where pulse energies are low, e.g. 0.2 joules, and the fiber tip to target distance is considerable, e.g. 1 mm, most or all of the laser energy may be consumed in simply boiling water.

Prior art has addressed this issue for pulsed lasers by providing closely spaced or overlapping pulses: a small pulse to produce a vapor bubble though which a second, larger pulse may pass with minimal interaction with the surgical irrigant. As taught by U.S. Pat. No. 5,321,715, laser energy traveling in a liquid medium toward a target tissue will be absorbed, but that absorption may be less than expected due to the "Moses Effect". As in the Biblical reference, the waters are parted by a first component of the pulse energy in producing a vapor bubble (Moses bubble) within the liquid medium. The remaining pulse energy passes through the far less attenuating medium of the bubble, resulting in higher that initially anticipated coupling of energy to the target.

The '715 patent describes a pulse format to increase the amount of laser energy which will arrive at the target tissue. According to the description, a first short and low energy initiation pulse is generated in order to create a bubble, followed by a higher energy treatment pulse. The second (treatment) pulse, when it passes through the created and now-formed bubble, experiences a lower absorption rate due to the presence of the bubble (and the absence of liquid). Moreover, the '715 patent teaches that the energy of the first bubble initiation pulse be sufficient enough to initiate the formation of a vapor bubble. The bubble thus formed may then displace a substantial portion of the fluid medium between a tip of a laser fiber and a target tissue.

Additional prior art has concentrated upon optimization of the Moses Effect. U.S. Pat. No. 5,632,739 teaches that a delay between a bubble initiation pulse and a treatment pulse is chosen so that the second pulse is emitted when the bubble size and corresponding amount of displaced fluid is at its maximum extent. U.S. Pat. No. 9,895,196 teaches optimization of reduced retropulsion (movement of target calculus away from the laser pulse source) in alternative timing of laser pulses.

Retropulsion is a is a phenomenon that is highly variable in real-world surgery and appears to be a function of laser pulse energy and repetition rate as well as fiber tip to target distance, stone composition and stone location in the anatomical region. In timing the second laser pulse for delivery just as the bubble begins to collapse, the '196 patent teaches the stone will be drawn in to the beam at the same time it is repulsed by the second pulse, maintaining the stone at a fixed distance from the fiber, where the separation of fiber and target is critical to the optimization of energy coupling efficiency.

U.S. Pat. No. 6,998,567 teaches the production of a multi-pulse train primarily for improved energy efficiency in generating the laser pulses, but with a mention of overlapping pulses for enhancing acoustic and thermal effects upon the target.

SUMMARY

In accordance with aspects of the present invention, a dual wavelength, dual mode surgical laser is provided. The system is comprised of a standard "holmium" surgical laser generating pulses of energy for ablation or fragmentation of biological calculi or tissue, the output energy of which is overlaid on a continuous wave (CW) laser output at or very near the 1930 nm absorption maximum for water.

A first embodiment is a surgical method that includes establishing a steam bubble between a fiber tip and a surgical target; maintaining the steam bubble by providing a low-power, continuous-wave laser emission; and then delivering to the surgical target through the steam bubble a therapeutic laser emission providing ablation of the surgical target.

A second embodiment is a surgical device that includes a therapeutic laser emission source having a power output of greater than 10 Watts, 25 Watts, 50 Watts, or 100 Watts; a continuous-wave laser emission source having a power output of less than 5 Watts, less than 2 Watts, less than 1 Watt, less than 0.5 Watts, or less than 0.2 Watts; a low angle therapeutic laser emission launch adapted to provide a therapeutic laser emission to a core of an optical fiber; a high angle continuous-wave laser emission launch adapted to provide a continuous-wave laser emission to the optical fiber with a launch angle of greater than about 4°, 8°, 12°, or 15°; wherein the low-angle and high-angle of the respective launches are with respect to a longitudinal axis of the optical fiber.

BRIEF DESCRIPTION OF THE FIGURES

For a more complete understanding of the disclosure, reference should be made to the following detailed description and accompanying drawing figures wherein:

FIG. 4 shows three surgical fiber output beam profiles relevant to the invention.

While specific embodiments are illustrated in the figures, with the understanding that the disclosure is intended to be illustrative, these embodiments are not intended to limit the invention described and illustrated herein.

DETAILED DESCRIPTION

Objects, features, and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

Herein, the use of the word "a" or "an" when used in conjunction with the term "comprising" in the claims and/or the specification may mean "one," but it is also consistent with the meaning of "one or more," "at least one," and "one or more than one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

Herein are provided components for and an improved surgical laser system for coupling infrared surgical energy to biological targets within a water-based medium.

Figure 1:
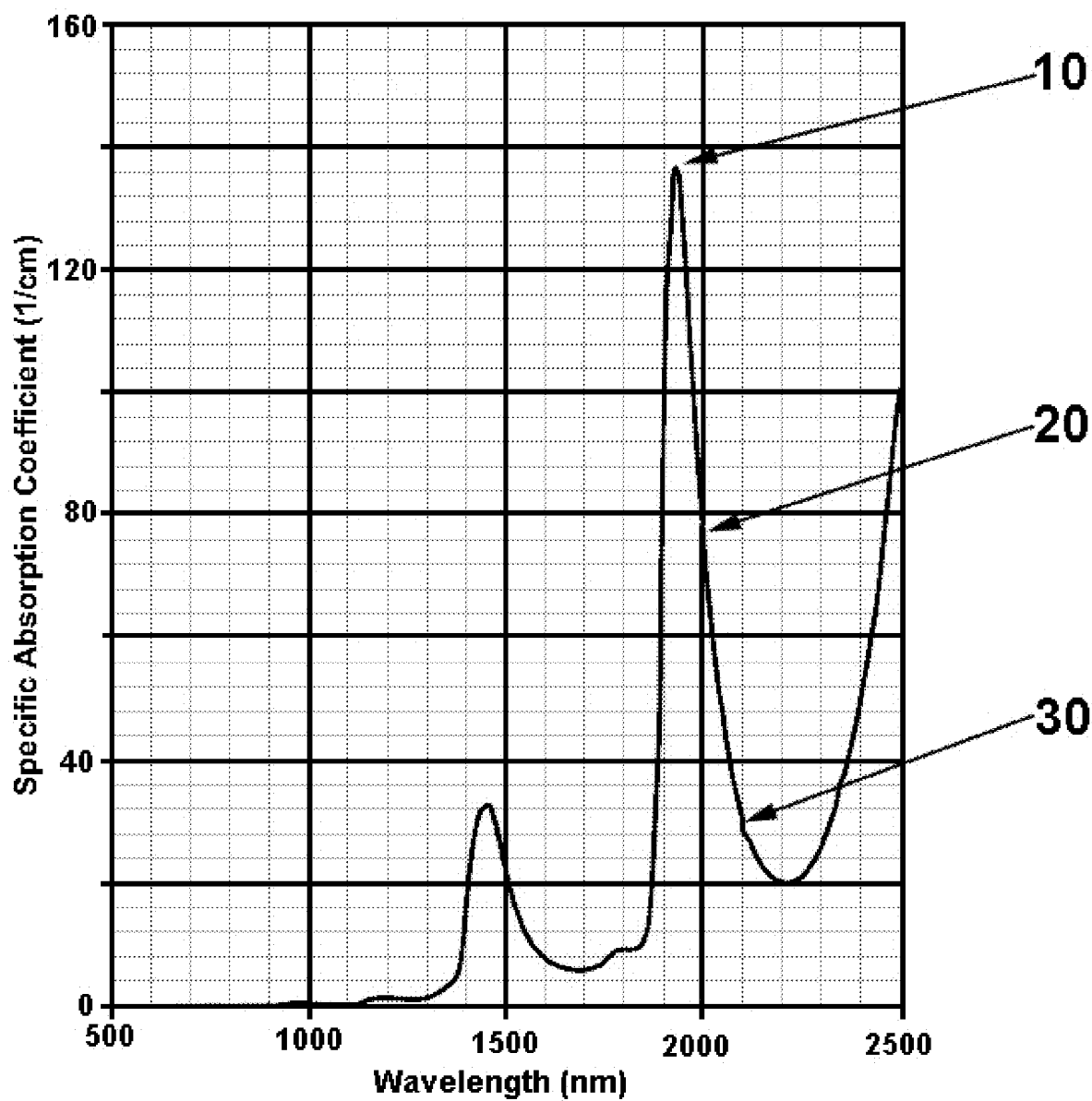
FIG. 1 is a graph of infrared light absorption in water.

FIG. 1 depicts the absorption spectrum of water within the wavelength range of interest to this invention, where 10 represents the peak absorption at approximately 1930 nm, 20 represents the absorption at the nominal wavelength for broadly used "thulium" lasers, and 30 represents the absorption at the nominal wavelength for common "holmium" lasers. For reference, it should be noted that holmium lasers produce a pulsed output, typically ranging from 0.2 Joules (J) per pulse to 6 J per pulse at a repetition rate ranging from 5 Hertz (Hz) to 60 Hz and average power ranging from approximately 12 Watts (W) to 120 W, maximum, where thulium lasers are typically continuous output lasers (continuous wave, or CW) with average powers of 100 W to 250 W. The laser energy is generally coupled to an optical fiber for delivery to the surgical target within the body.

Where pulse energies are low, e.g. 0.2 joules per pulse, and the distance between the optical fiber output tip and kidney stone is large, e.g. 1 mm or greater, essentially none of the surgical energy arrives at the stone. Where pulse energies are high and the distance between the optical fiber tip and surgical target is small or the fiber is in contact with the surgical target, the vast majority of the surgical energy arrives at the stone, at least for the first pulse. In real world surgery, however, the surgical targets irregular and often in violent motion, agitated by the expansion and collapse of vapor bubbles, making intimate contact between the fiber tip and the target impossible to maintain.

The infrared output of continuous wave (CW) surgical lasers used for soft tissue ablation and resection is similarly absorbed, but being CW, the absorption is incomplete at surgical powers. While incomplete, energy loss to absorption by water is sufficient to cause problems. A continuous stream of bubbles may obscure clear visualization of the surgical site under treatment and in order to maintain surgical efficacy, fibers are maintained in contact, or very near contact, with soft tissues to the disadvantage of fiber lifetime and performance.

Figure 2:
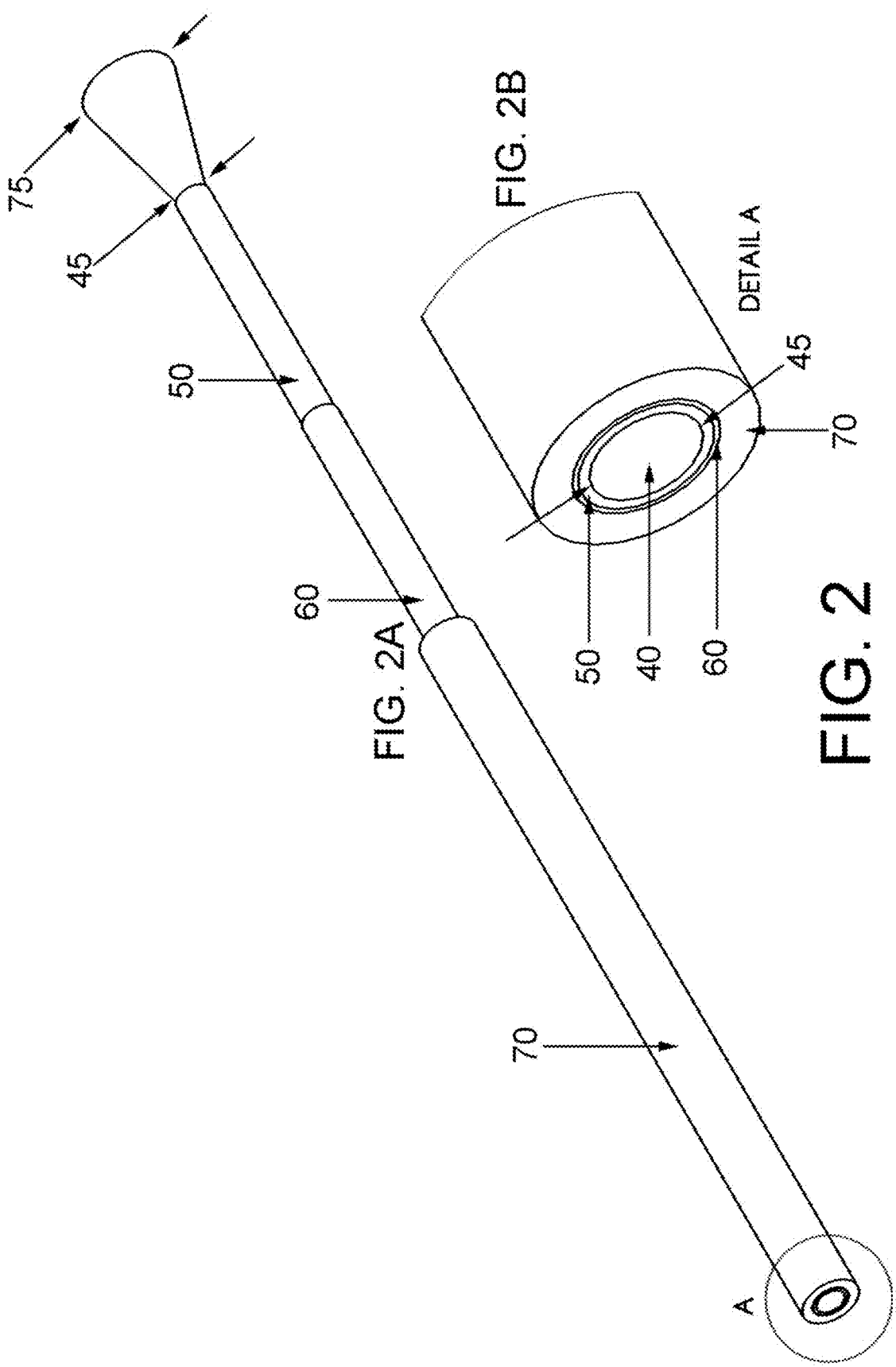
FIG. 2 is an isometric representation of a typical laser lithotripsy fiber construction with divergent output (FIG. 2A) and detail of the input end (FIG. 2B)

First principles of optics and physical chemistry may be used to approximate the energy loss due to vapor bubble formation. Where the radiant intensity is as high as possible—with energy delivered via the smallest diameter, least divergent optical fibers that are compatible with cleared surgical lasers (0.2 mm core, 12.7° half angle divergence, assuming mode filled condition)—the volume of water interacting with the laser pulse/beam, between the fiber exit surface and the kidney stone, is approximated by a frusto-conical solid FIG. 2 with volume V given by $$V = \frac{\pi h}{3}(r_1^2 + r_1 r_2 + r_2^2),$$

where h is the fiber tip to target distance, $r_1$ is half the diameter 75 and $r_2$ is half the diameter 45 and where $r_1=[r_2+2 (\tan 12.7)]/2$. For h=1.0 mm separation and a 0.2 mm core 40 fiber, $r_1=0.325$ mm, $r_2=0.1$ mm so V=0.155 mm$^2$.

Assuming the temperature of the water is normal biological temperature (37° C.) and approximating the density of water at 1 gram (g) per cm$^3$ for 0.000155 g of water in the conical frustum, given a heat of vaporization of 2257 J/g and approximating the specific heat of water for the relevant temperature range of 37° C. to 100° C. at 4.187 J/° C., we arrive at approximately 0.39 J required to vaporize the "Moses volume". The larger the fiber diameter, the larger the Moses volume and the greater the energy required to vaporize the path to the stone. The fluid dynamics and thermal gradients within the surgical field are admittedly ignored in this approximation, but practice proves the approximation valid; in that 0.2 mm is the smallest commonly available fiber core diameter, the lowest two settings for most holmium lasers, 0.2 J and 0.4 J, prove ineffective at 1 mm or greater fiber tip to target distances.

U.S. Pat. No. 9,895,196 teaches provision of two laser pulses, a first pulse optimized to open a vapor pathway based upon the fiber tip to target separation, followed by a second pulse that is timed to pass just as the Moses bubble is beginning to collapse such that the retropulsion of the target caused by the expansion of the bubble is revered in its collapse. While this strategy has theoretical value, it is impractical to precisely measure fiber tip to target distance for each and every pulse to be delivered in laser lithotripsy for optimization of each Moses bubble; fiber position is under manual control, fiber tips degrade, stone surfaces are irregular and stones dance about, often violently, while ablating and fragmenting. It would be simpler to simply provide a highly absorbed, continuous wave (CW) signal to maintain a "Moses corridor" between the fiber and target for delivery of unimpeded surgical pulses.

A first embodiment of an improved surgical laser system is comprised of a standard, high pulse energy, flashlamp or diode pumped, solid state gain medium combined with a low power, diode or DPSS laser with continuous emission at or adjacent the peak absorptivity of water at ~1930 nm, and optically coupled to a fiber optic laser energy delivery device. The combination of the two lasers may be accomplished via a crystalline beam combiner, rotating mirrors or other means known in the art.

The power of the diode laser is selected to be sufficient to establish and maintain a vapor bubble between the fiber delivery device output tip and the surgical target ("gap"). This vapor bubble need not bridge the entire gap, but may fall short in some cases where the gap varies considerably with time, yet should be sufficient to substantially reduce the chaotic bubble formation/collapse cycle generally seen in pulse infrared laser surgery.

Ideally the divergence of the CW beam is greater than the divergence of the therapeutic pulses. Optical fiber constructions FIG. 2 used in laser lithotripsy offer a convenient means of ensuring such. The low [OH] synthetic fused silica core 40 is clad 50 with fluorine-doped, low [OH] fused silica having a slightly lower refractive index than the core 40 material. Therapeutic laser pulses are contained within the core:cladding waveguide thus provided. At the long wavelengths and high peak pulse energies used in laser lithotripsy, however, some substantial evanescence typically extends beyond the glass cladding, sufficient to heat the fiber buffer 70 to beyond its glass transition temperature and, in some cases, melt or burn the buffer. A secondary containment is therefore provided in the form of a polymer cladding 60 with a refractive index lower than the glass cladding 50.

The polymer cladding produces a second fiber numerical aperture (NA) here higher off axis light rays may be propagated. The efficiency of propagation within the higher (or secondary) NA is a function of absorption and scatter of light within the core 40, the fluorine-doped glass cladding 50 and, to some degree, the polymer cladding 60. The polymers used, e.g. optical silicones, fluoroacrylates, fluorourethances, generally absorb and scatter long wavelength light more than glasses: the longer the wavelength, the more absorption and scatter.

Figure 3:
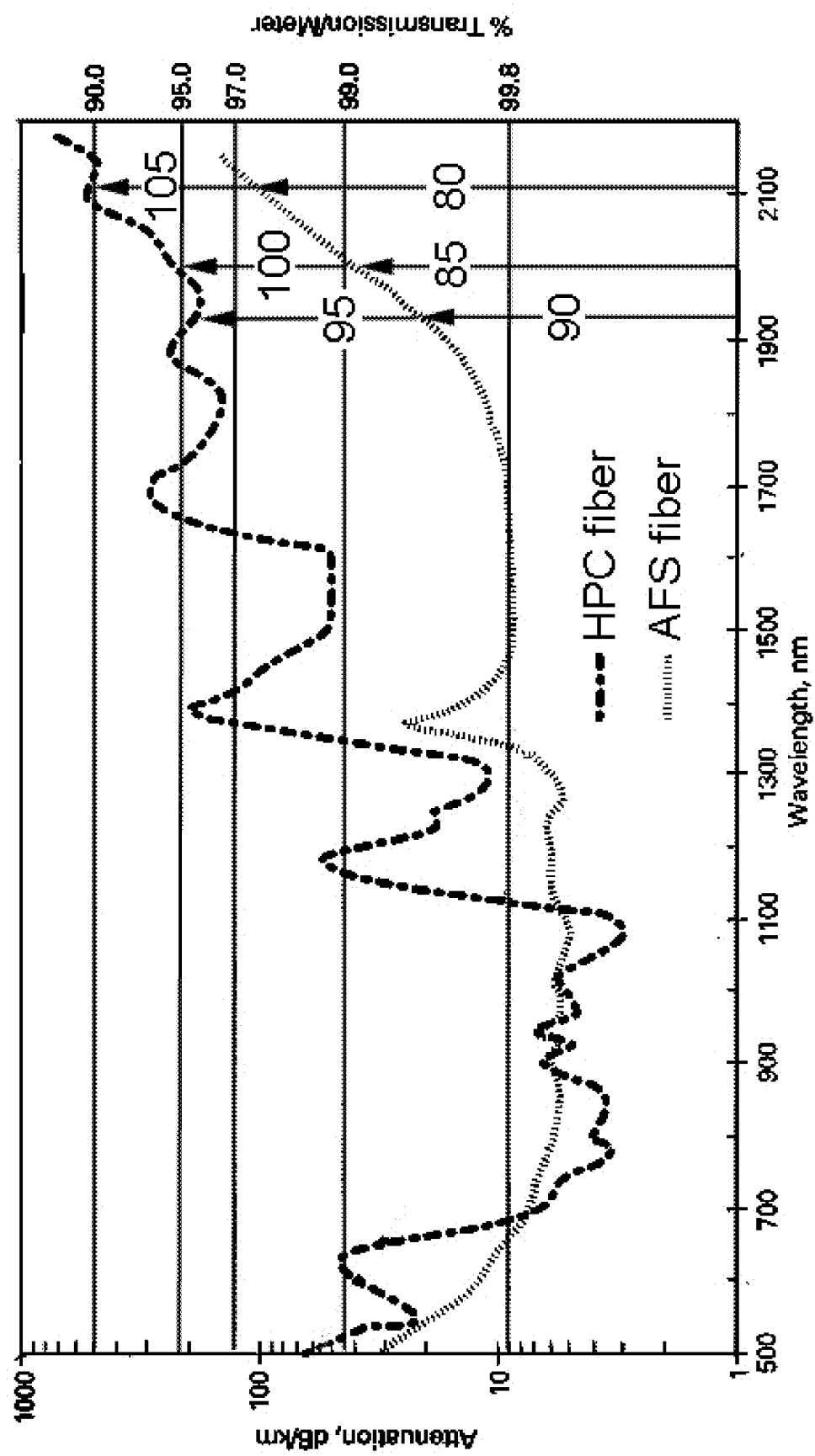
FIG. 3 depicts the attenuation/transmission spectra for the primary NA (AFS fiber) and secondary NA (HPC fiber) for fiber of the type used in laser lithotripsy surgery.

As may be seen in FIG. 3, holmium wavelengths, e.g. 2140 nm 80, nudge up against the longest practical wavelength that can safely be delivered by All Fused Silica (AFS) optical fiber, under high peak power and in tortuous paths. Thulium laser wavelengths 85 are shorter and present far less of a challenge to the fiber construction due to much lower peak powers produced in CW lasers. The CW Moses corridor producing laser at 1930 nm 90 is an even shorter wavelength than thulium and the power required to open and maintain the Moses corridor is substantially lower than that required at thulium's wavelength, principally due to the almost 2-fold larger specific absorption coefficient for water at 1930 nm 10 versus thulium at 2000 nm 20 FIG. 1. The 1930 nm laser may accordingly be carried within the secondary NA of the fiber 95, with a numerical aperture equivalent to polymer clad or Hard Polymer Clad (HPC) fiber, such that divergence of the Moses corridor maintaining beam is higher than the therapeutic pulse divergence.

Holmium laser energy is poorly contained by Hard Polymer Cladding (and other common organic cladding materials) 105 due to relatively strong interaction of the wavelengths with the polymers and high peak pulse powers. HPC fiber coatings contain thulium laser energy 100 better than holmium laser energy 105 albeit poorly due to the high powers typically used in surgery. The power of the Moses corridor laser, however, is considerably lower than that required for surgery, such that even relatively significant interaction with the HPC coating 95 does not risk overheating the fiber.

It is therefore critical to contain surgical wavelengths to the primary NA to avoid overheating the fiber coatings (polymer cladding and buffer) that leads to a catastrophic failure mode known as "burn through" in the surgical art. Surgical energy is launched into the primary NA with maximum angles below the maximum acceptance angle (approximately 12.5° off the longitudinal axis for a 0.22 primary NA), resulting in a semi-Gaussian output beam profile FIG. 4A where the fiber is relaxed (not under significant bending stress). Where surgical access requires the fiber to traverse a tortuous path, as is typical in laser URS (Ureteroscopy), output beam profiles become more flattened FIG. 4B with laser energy carried relatively evenly throughout the primary NA. Bending beyond the optical bend limit minimum causes some surgical energy to leak into the secondary NA at angles beyond the primary NA containment capacity.

Ideally, the Moses corridor maintaining beam is carried and/or delivered as an annular beam rather than a cylindrical solid. An annulus is all that is required to maintain the Moses corridor once it has been established, either by duration of interaction with the aqueous environment or by passage of the first therapeutic laser pulse. An annular beam may be established by skew launch into the fiber, optical conditioning and other means known in the art, such as off axis launch FIG. 4C. In that the Moses corridor maintaining CW laser power is very low compared to the surgical laser power, the power loss to absorption in the polymer cladding remains well below the failure threshold, even where the annular character of propagation is enhanced in bending stress during surgery.

Herewith, another embodiment is a surgical method that includes establishing a steam bubble between a fiber tip and a surgical target; maintaining the steam bubble by providing a low-power, continuous-wave laser emission; and then delivering to the surgical target through the steam bubble a therapeutic laser emission providing ablation of the surgical target. Notably, this method reduces or eliminates any therapeutic laser power lost to the formation of a bubble between the fiber tip and the surgical target. Preferably, greater than 90%, 92%, 94%, 96%, 98%, 99%, 99.5%, or 99.9% of the power output from the therapeutic laser emission reaches the surgical target. More preferably, no therapeutic laser emission power is lost by absorption of water between the fiber tip and the surgical target.

Herein, the steam bubble is preferably maintained by laser emissions from the fiber tip, the laser being a low-power, continuous-wave laser that is, generally, considered to be of no therapeutic use. Notably, the term low-power means that the continuous-wave laser (and the CW laser emissions) have insufficient power to ablate a surgical target; more preferably, low-power means that the CW laser and emissions have insufficient power to affect a physiochemical change in the surgical target; for example, insufficient power to cauterize, ablate, facilitate a Malliard reaction, denature proteins, or cause the pulverization or the disunification by impact (implosion) of the surgical target. Importantly when used in laser lithotripsy, the low-power means that the CW laser and emissions fail to cause cavitation effects and fail to lead to stone/calculi destruction. Notably, a low-power CW laser (and emissions) provide no "plasma bubble" or similar cavitation that is believed to lead to ablation effects.

Preferably, the CW laser and emissions are of sufficient power to vaporize or maintain the vaporization of water at the fiber tip. In one example, the continuous-wave laser emission has a power output of less than 5 Watts, less than 2 W, less than 1 W, less than 0.5 W, less than 0.4 W, less than 0.3 W, less than 0.25 W, or less than 0.2 W. Accordingly, it is preferred that the continuous-wave laser emission has a power output that is insufficient to affect ablation of the surgical target, preferably insufficient to affect a change in the surgical target. In one instance, the continuous-wave laser emission has a power output that is sufficient to dehydrate the surgical target.

In one instance, the continuous-wave laser emission has a divergent emission from the fiber tip. In another instance, the continuous-wave laser emission has an annular beam profile. In still another instance, the continuous-wave laser emission has a beam profile that does not significantly overlap with the beam profile of the therapeutic laser emission (e.g., overlap is less than 20%, 15%, 10%, 5%).

In one particularly preferably instance, the continuous-wave laser emission has an emissions wavelength of about 1930 nm. Herein, the emissions wavelength can be 1930 nm±30 nm, ±20 nm, or ±10 nm.

Herein, the continuous-wave laser emission is provided by one or more laser diodes or diode-pumped solid-state lasers coupled to the fiber tip. That is, the continuous-wave laser emission is that of a CW laser diode or diodes, or a diode-pumped solid-state laser.

In another instance, the ablation of the surgical target is provided by therapeutic laser emissions from the fiber tip, this laser being a high-power, pulsed laser that is commonly found in therapeutic use (e.g., a holmium laser or a thulium laser). In one example, the therapeutic laser emission has a wavelength greater than 1960 nm, 1970 nm, 1980 nm, 1990 nm, or 2000 nm. Specific wavelengths can be those provided by, for example, a holmium laser, a thulium laser, or another high wavelength surgical laser. In another example, the therapeutic laser emission has a power output of greater than 5 Watts, 10 W, 25 W, 50 W, or 100 W.

Preferably, the therapeutic laser emission is delivered as a plurality of laser pulses. In one instance, the plurality of laser pulses is at about 5 Hz, 10 Hz, 15 Hz, 20 Hz, 25 Hz, 30 Hz, 35 Hz, 40 Hz, 45 Hz, 50 Hz, 55 Hz or 60 Hz; in another instance, the plurality of laser pulses is provided between about 10 Hz and about 2 KHz.

Herein, the term ablation means the fragmentation, disintegration, abscission, violent expansion of a hard surgical target (e.g., urinary, biliary, or salivary calculi) and/or the vaporization, excision, incision of a soft surgical target. Notably, the term ablation does not include the pulverization or the disunification by impact (implosion) of a surgical target by applying a shock wave to the target surface. In one instance, the ablation of the surgical target is provided by the rapid expansion of water within the surgical target. Accordingly, the surgical target is preferably porous and/or hydrated—containing sufficient water to facilitate the ablation (e.g., in the pores of the surgical target). More preferably, the surgical target is not dehydrated (e.g., dry) or sufficiently non-porous that the target retains little to no water. In another instance, the ablation of the surgical target includes the rapid expansion and contraction of water within the surgical target. These rapid changes within the surgical target, preferably, cause the disintegrating the surgical target (e.g., causing the surgical target to fracture and powder), preferably resulting in a fine powder that is carried from the surgical site (the location of the surgical target) by a water lavage.

In another instance, the therapeutic laser emission can be delivered at a wavelength that is less than 500 nm. In this instance, it is preferable that the surgical target is vaporized instead of disintegrated. Notably, at below 500 nm, the wavelength(s) are preferably chosen to be one or more endogenic chromophores (e.g., oxy- or deoxy-hemoglobin). In one example, the therapeutic laser emission is a combination of a plurality of emissions each having a wavelength less than 500 nm, preferably chosen to be one or more endogenic chromophores, degradation products, or thermal product.

Notably, the method describe herein is useful in orthoscopic, lithotripsic, or similar laser surgical procedure, but open, percutaneous or endoscopic access. Accordingly, the continuous-wave laser emission and the therapeutic laser emission are provided via an optical fiber. Preferably, the optical fiber has a fused silica core, the fused silica core clad with a fluorine doped silica cladding, the fluorine doped silica cladding having a polymer cladding; wherein the therapeutic laser emission is contained within the fused silica core by the fluorine doped silica cladding. In one particularly preferable instance, the continuous-wave laser emission is contained within the fluorine doped silica cladding by the polymer cladding. Notably, the process can include providing the CW laser emission to the optical fiber (from the CW laser) with a high launch angle, that is, along a path that is not commensurate with the fiber's longitudinal axis. In one instance, the continuous-wave laser emission it provided to the optical fiber with a high angle launch that is greater than about 4°, about 8°, about 10°, about 12.5°, or about 15° off the fiber longitudinal axis.

Figure 5:
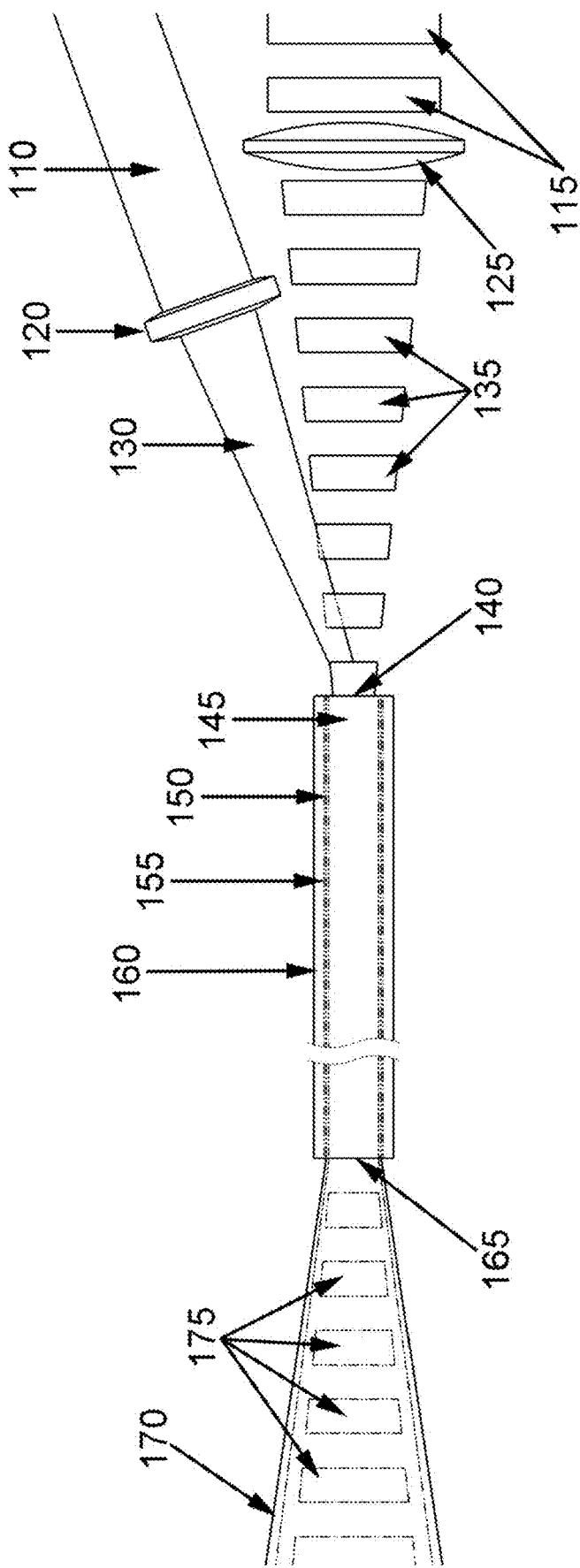
FIG. 5 illustrates an off-axis launch of a continuous-wave laser emission into a fiber with a pulsed therapeutic laser, and the output beams.

FIG. 5 illustrates the off-axis launch of the CW Moses corridor producing beam 110 with respect to the on-axis launch of the therapeutic, pulsed beam 115 according to embodiments disclosed. The CW beam 110 is focused by a lens 120 or lenses as is the pulsed beam 115 at 125, producing a converging CW beam 130 and converging pulsed beam 135, both imparting the fiber input aperture 140 but where the pulsed beam 115 is centrosymmetric about the fiber longitudinal axis and the CW beam 110 is not. The pulsed energy is contained within the fiber core 145 as meridional and skew rays where the CW beam may be contained within the core 145 as skew rays, or the predominantly within the glass cladding 150 as skew rays, dependent upon the off-axis angle 175 of the CW launch and the refractive indices of the core 145, glass cladding 150 and the polymer cladding 155. A buffer coating 160 is depicted for completeness.

Launching the CW, Moses corridor beam 110/130 is skew rays produces a predominantly annular output beam 170 (FIG. 4C) upon exiting the fiber delivery aperture 165 whereas launching the pulsed, therapeutic beam 115/125 on the fiber axis produces a semi-Gaussian FIG. 4A or essentially top-hat FIG. 4B beam upon exiting the fiber delivery aperture 165.

An important feature of the current method is the formation or establishment of the stream bubble between the fiber tip and the surgical target. Notably, the stream bubble can be established by providing the continuous-wave laser emission and/or the therapeutic laser emission to water positioned between the fiber tip and the surgical target. In instances wherein the CW laser emission is insufficient to generate a stream bubble of sufficient size, the CW laser and the therapeutic laser can be used in tandem. Alternatively, the steam bubble can be established by a pulse of the therapeutic laser and then maintained by the CW laser. A variable length or power pulse of the therapeutic laser. Examples of variable length and power pulses are known in the art for the generation of steam bubbles prior to the firing of (fully strength) therapeutic pulses.

Notably, the evaporation of the water between the fiber tip and the surgical target requires sufficient power. While the total power necessary is based on the distance between the fiber tip and the surgical target as well as the fiber diameter; generally, the steam bubble can be established by providing a power output of greater than 1 Watt, 2 Watts, 3 Watts, 4 Watts, 5 Watts, 6 Watts, 7 Watts, 8 Watts, 9 Watts, or 10 Watts.

In one instance where the continuous-wave laser emission has an annular beam profile, the steam bubble is established by therapeutic laser emission. Notably, if the annular beam profile of the CW laser emission is sufficiently broad, this emission would leave an un-vaporized portion of water between the fiber tip and the surgical target, in such a circumstance, it is preferably to utilize a therapeutic pulse or a therapeutic pulse with the CW emissions to generate the steam bubble. That is, establishing the steam bubble can include providing the continuous-wave laser emission and the therapeutic laser emission, whereby the therapeutic laser emission eliminates residual water between the fiber tip and the surgical target, and whereby the continuous-wave laser emission maintains the steam bubble.

In another instance, the volume and number of stream bubbles is relatively constant during the surgical process. In one example, the volume of the steam bubble stays relatively constant throughout the ablation of the surgical target. Preferably, the volume of the steam bubble changes less than 50 vol. %, less than 40 vol. %, less than 30 vol. %, less than 25 vol. %, less than 20 vol. %, less than 15 vol. %, less than 10 vol. % while delivering the therapeutic laser emission to the surgical target. Accordingly, there is not a large displacement of material (e.g., water) while delivering the therapeutic laser emission. In one instance, this relatively constant volume reduces retropulsion or the repulsion of the surgical target during application of the therapeutic laser emission. While some retropulsion may occur due to the ablation of the surgical target, preferably, any retropulsion caused by the formation and collapse of bubbles between the fiber tip and the surgical target are eliminated. That is, eliminated by the maintenance of a single steam bubble between the fiber tip and the surgical target.

Preferably, the steam bubble is adjacent to the surgical target. That is, the steam bubble preferably occupies the volume between the fiber tip and the surgical target and thereby provides a gaseous beam path for the therapeutic laser. In instances, wherein the steam bubble is not adjacent to the surgical target but is proximal thereto, the therapeutic laser emission preferably eliminates any residual water between the steam bubble and the surgical target. Preferably, once the therapeutic laser emission eliminates the residual water the CW laser emission maintains the steam bubble from the fiber tip to the surgical target. In such an example, the therapeutic laser emission can have a power output of greater than 10 W, 25 W, 50 W, or 100 W at the fiber tip and the maintenance of the steam bubble by the CW laser emission prevents a reduction of the power output between the fiber tip and the surgical target. In instances wherein the CW laser is insufficient to maintain the steam bubble for the full distance from the fiber tip to the surgical target, the steam bubble prevents a large reduction of power and prevents or reduces the retropulsion of the surgical target. More preferably, when the CW laser permits a small portion of water to contact the surface of the surgical target, the interaction of this surface water with the therapeutic laser emission aids in the ablation of the surgical target and/or aids in the cleaning of the surgical target surface during ablation.

Another instance is a surgical device that includes a therapeutic laser emission source having a power output of greater than 10 Watts, 25 Watts, 50 Watts, or 100 Watts; and a continuous-wave laser emission source having a power output of less than 5 Watts, less than 2 Watts, less than 1 Watt, less than 0.5 Watts, or less than 0.2 Watts. The surgical device further includes a low-angle therapeutic laser emission launch adapted to provide a therapeutic laser emission to a core of an optical fiber with a launch angle of less than about 4°, 3°, 2°, or 1°; and a high-angle continuous-wave laser emission launch adapted to provide a continuous-wave laser emission to the optical fiber with a launch angle of greater than about 4°, 8°, 12°, or 15°. That is, the therapeutic laser and the CW laser are provided to the fiber with different launch angles. Notably, the low-angle and high-angle of the respective launches are with respect to a longitudinal axis of the optical fiber.

Preferably, the surgical device includes an optical fiber having a fused silica core, the fused silica core clad with a fluorine doped silica cladding, the fluorine doped silica cladding having a polymer cladding.

In one instance, the surgical device includes a holmium laser or a thulium laser as the therapeutic laser emission source. In another instance, the continuous-wave laser emission source is one or more laser diodes or diode-pumped solid-state lasers, the emission source having an emissions wavelength of 1930±30 nm, ±20 nm, or ±10 nm.

Another benefit of using a low power, CW laser for maintenance of the Moses Corridor as opposed to using the therapeutic laser wavelength is a reduction in thermal stress on surrounding tissues that are in contact with the surgical irrigant. Essentially all of the laser energy delivered to a kidney stone results in the heating of the water, some directly in forming the Moses vapor bubble, and the rest indirectly by heating the kidney stone which transfers that heat to the water my various thermal mechanisms. The time scale of transfer is irrelevant in surgical treatment timeframes that range from a dozen seconds to over a minute of continuous lasing. What differs is the fraction of the total energy that produces therapeutic benefit.

The length of time a surgeon will continuously activate the laser is largely dependent upon the results observed. If little material is removed with each pulse, lasing intervals tend to be long as the surgeon concentrates the laser energy upon the stone mass. Where the stone is moving—away from the fiber or dancing about in what is known in the art as "popcorn" motion—only random pulses may have therapeutic effect. Minimization of motion enhances surgical efficacy for a given amount of power applied. The lower the amount of total energy required performing a procedure, the less the chance of the patient's surrounding tissue suffers inadvertent thermal damage.

A 0.242 mm core optical fiber delivering 1 J pulses at 40 Hz can raise the temperature of the surgical irrigant to over 70° C. within one minute, beyond the denaturing temperature of most proteins; as more powerful lasers are approved for surgical use, the risk of patient injury due to thermal damage to tissues increases. A 0.2 mm fiber, at 1 mm separation between fiber tip and stone, wastes almost 40% of a 1 J pulse in heating the surgical irrigant, or almost 16 W at 40 Hz: the larger the fiber, the greater the inefficiency. The invention described herein may maintain a Moses Corridor with less than 5 watts, at any power setting and for any size fiber.

While the compositions and methods of this invention have been described in terms of preferred embodiments, it will be apparent to those of skill in the art that variations may be applied to the compositions and/or methods in the steps or in the sequence of steps of the method described herein without departing from the concept, spirit and scope of the invention. More specifically, it will be apparent that certain agents that are both chemically and physically related may be substituted for the agents described herein while the same or similar results would be achieved. All such similar substitutes and modifications apparent to those skilled in the art are deemed to be within the spirit, scope and concept of the invention as defined by the appended claims.

What is claimed:

1. A surgical method comprising: establishing a steam bubble between a fiber tip and a surgical target; maintaining the steam bubble by providing a low-power, continuous-wave laser emission; and then delivering to the surgical target through the steam bubble a therapeutic laser emission; wherein the therapeutic laser emission provides ablation of the surgical target.

2. The surgical method of claim 1, wherein the continuous-wave laser emission is diverging from the fiber tip.

3. The surgical method of claim 1, wherein the continuous-wave laser emission has an annular beam profile.

4. The surgical method of claim 1, wherein the continuous-wave laser emission has a wavelength of 1930±30 nm and a power output of less than 5 Watts.

5. The surgical method of claim 1, wherein the therapeutic laser emission has a wavelength greater than 1960 nm and a power output of greater than 10 Watts.

6. The surgical method of claim 1, wherein the therapeutic laser emission has a wavelength shorter than 500 nm.

7. The surgical method of claim 1, wherein the continuous-wave laser emission and the therapeutic laser emission are provided via an optical fiber having a fused silica core, the fused silica core clad with a fluorine doped silica cladding, the fluorine doped silica cladding having a polymer cladding; wherein the therapeutic laser emission is contained within the fused silica core by the fluorine doped silica cladding.

8. The surgical method of claim 7, further comprising providing the continuous-wave laser emission to the optical fiber with a high-angle launch of greater than 4° off a longitudinal axis of the optical fiber.

9. The surgical method of claim 1, wherein establishing the steam bubble includes providing at least one of the continuous-wave laser emission and the therapeutic laser emission to water disposed between the fiber tip and the surgical target.

10. The surgical method of claim 9, wherein the continuous-wave laser emission has an annular beam profile, and wherein the steam bubble is established by said therapeutic laser emission.

11. The surgical method of claim 1, wherein a volume of the steam bubble changes less than 50 vol. % while delivering the therapeutic laser emission to the surgical target.

12. The surgical method of claim 1, wherein the method provides a single steam bubble.

13. The surgical method of claim 1, wherein the steam bubble is adjacent to the surgical target.

14. The surgical method of claim 1, wherein said maintaining the steam bubble reduces retropulsion.

15. The surgical method of claim 1, wherein the therapeutic laser emission has a power output of greater than 10 Watts at the fiber tip; and wherein said maintaining the steam bubble prevents a reduction of a power output between the fiber tip and the surgical target.

16. A surgical device comprising:
a therapeutic laser emission source having a power output of greater than 10 Watts;
a continuous-wave laser emission source having a power output of less than 5 Watts;
a low-angle therapeutic laser emission launch adapted to couple a therapeutic laser emission to a core of an optical fiber; and
a high-angle continuous-wave laser emission launch adapted to provide a continuous-wave laser emission to the optical fiber with a launch angle of greater than 4 degrees;
wherein the low-angle and high-angle of respective launches are measured with respect to a longitudinal axis of the optical fiber.

17. The surgical device of claim 16, further comprising the optical fiber having a fused silica core, the fused silica core clad with a fluorine-doped silica cladding, the fluorine-doped silica cladding having a polymer cladding.

18. The surgical device of claim 16, wherein the therapeutic laser emission source is a holmium laser or a thulium laser.

19. The surgical device of claim 16, wherein the continuous-wave laser emission source is one or more of laser diodes or diode-pumped solid-state lasers, the continuous-wave laser emission source having an emissions wavelength of 1930±30 nm.

20. The surgical device of claim 17, wherein
the surgical device is configured to carry the continuous-wave laser emission in the fluorine-doped silica cladding.

* * * * *